United States Patent [19]

Foricher et al.

[11] Patent Number: 5,030,739

[45] Date of Patent: Jul. 9, 1991

[54] PROCESS FOR THE CATALYTIC OXIDATION OF ISOPRENOIDS HAVING ALLYLIC GROUPS

[75] Inventors: Joseph Foricher, Mulhouse, France; Claude Fürbringer, Riehen; Karlheinz Pfoertner, Basel, both of Switzerland

[73] Assignee: Hoffman-La Roche Inc., Nutley, N.J.

[21] Appl. No.: 576,096

[22] Filed: Aug. 31, 1990

Related U.S. Application Data

[63] Continuation of Ser. No. 453,146, Dec. 13, 1989, abandoned, which is a continuation of Ser. No. 849,340, Apr. 8, 1986, abandoned.

[30] Foreign Application Priority Data

Apr. 17, 1985 [CH] Switzerland .......................... 1637/85

[51] Int. Cl.$^5$ ......................... C07C 407/00; C07J 9/00
[52] U.S. Cl. ..................... 552/542; 560/113; 560/249; 568/344; 568/346; 568/347; 568/356; 568/357; 568/374; 568/570; 568/571; 568/857; 585/432
[58] Field of Search ................. 560/113, 249; 568/570, 568/571; 552/542

[56] References Cited

U.S. PATENT DOCUMENTS

| | | | |
|---|---|---|---|
| 2,911,442 | 11/1959 | Bain et al. ......................... | 568/344 X |
| 4,104,312 | 8/1978 | Angstadt et al. ............... | 560/126 X |
| 4,209,450 | 6/1980 | Jaedicke et al. I ............. | 560/126 X |
| 4,393,243 | 7/1983 | Lohri I ................................ | 568/344 |

FOREIGN PATENT DOCUMENTS

| | | | |
|---|---|---|---|
| 36651 | 9/1981 | European Pat. Off. ............ | 560/126 |
| 0067258 | 12/1982 | European Pat. Off. ............ | 560/126 |
| 2704406 | 8/1980 | Fed. Rep. of Germany ...... | 560/126 |

OTHER PUBLICATIONS

Muller, R. et al., Helv. Chim. Acta 61:28881-87 (1978).
Becher E. et al., Helv. Chim. Acta 64:2419-35 (1981).
Chemical Abstracts 84:164279h (1976) Yoshimura et al.
Masui, M. et al., IJ. Chem. Soc. Chem. Commun. 479-480 (Feb. 1983).
Masui, M. et al., II Chem. Pharm. Bull. Commun 31:4209-11 (1983).
Sharma, C. S. et al., Synthesis, vol. 1974, 45-46 (Jan. 1974).
Sethi, S. et al., J Heterocycles 18:221-28 (1982).

*Primary Examiner*—Mary C. Lee
*Assistant Examiner*—Fiona T. Powers
*Attorney, Agent, or Firm*—George M. Gould; Bernard S. Leon; George W. Johnston

[57] ABSTRACT

The invention is directed to a process for the catalytic oxidation of an isoprenoid containing at least one allylic hydrogen atom, which process comprises reacting the isoprenoid with oxygen or an oxygen-containing gas in an inert solvent in the presence of a N-hydroxydicarboxylic acid imide of the formula

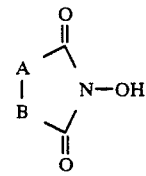

wherein A-B stands for $CH_2-CH_2$, $CH=CH$, an aromatic hydrocarbon residue or a group derived from one of these groups in which one or more hydrogen atoms is/are replaced by alkyl or halogen, to produce a primary of secondary hydroperoxide.

The process of the invention is suitable for the manufacture of steroids, vitamins, odorant substances, carotinoids and the like.

11 Claims, No Drawings 5,030,739

PROCESS FOR THE CATALYTIC OXIDATION OF ISOPRENOIDS HAVING ALLYLIC GROUPS

This application is a continuation of application Ser. No. 07/453,146, filed Dec. 13, 1989, now abandoned which is a continuation of Ser. No. 06/849,340, filed Apr. 8, 1986, now abandoned.

BACKGROUND OF THE INVENTION

The present invention is concerned with a process for the catalytic oxidation of allylic groups. Such reactions are fundamentally of great interest in organic chemistry since they are used in the most varied fields of application, e.g., in the manufacture of steroids, vitamins, odorant substances, carotinoids and the like.

Metal oxides, for example manganese dioxide, chromic acid or chromates, have frequently been used in the known art for the oxidation of allylic groups. Further, catalytic oxidations with oxygen or air are known, whereby metal compounds, for example cobalt, manganese, lanthanum or rhodium compounds, have been used as the catalysts.

However, the previously known processes frequently gave unsatisfactory yields and led to ecological damage by the resulting metal salts. Moreover, the products usually contained traces of metal compounds, which is undesirable especially in the manufacture of pharmaceuticals, food additives and feed additives.

SUMMARY OF THE INVENTION

The present invention is concerned with a novel process for the catalytic oxidation of isoprenoids, which possess an allylic group, with oxygen or an oxygen-containing gas.

DETAILED DESCRIPTION OF THE INVENTION

The process in accordance with the invention comprises oxidizing an ispreniod, which has at least one allylic hydrogen atom, in an inert ketone or ester in the presence of a N-hydroxydicarboxylic acid imide of the general formula

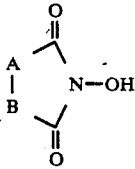

wherein A-B stands for —CH$_2$—CH$_2$—, —CH=CH—, an aromatic hydrocarbon residue or a group derived from one of these groups in which at least one hydrogen atom is replaced by alkyl or halogen, and, if desired, reducing a hydroperoxide obtained to the alcohol or dehydrating a primary or secondary hydroperoxide obtained to the carbonyl compound.

The process in accordance with the invention avoids the use of metal compounds and consequently also a contamination of the product by metal compounds. The catalysts of formula I which are used in accordance with the invention are comparatively harmless toxicologically. Moreover, as the catalyst can be recovered practically completely by simple means and can be reused the ecological damage is also considerably reduced. The process in accordance with the invention is, moreover, technically readily applicable and cheap, as it can be carried out especially even with air.

The term "alkyl" embraces in the scope of the present invention straight-chain and branched alkyl groups such as methyl, ethyl, propyl, isopropyl, butyl, isobutyl, t-butyl and the like.

The term "halogen" signifies in the scope of the present invention fluorine, chlorine, bromine or iodine, preferably chlorine.

The term "primary hydroperoxide" denotes compounds which have a hydroperoxymethyl group —CH$_2$—OOH and the term "secondary hydroperoxide" denotes compounds which have a hydroperoxymethylene group —CH(OOH)—.

The catalysts which are used in accordance with the invention are N-hydroxyimides of dicarboxylic acids, including those dicarboxylic acids which can form cyclic imides in accordance with formula I. The term "aromatic hydrocarbon" in formula I above includes diradicals derived from aromatic hydrocarbons such as benzene, naphthalene and the like, whereby the radical positions are in the ortho- or peri-position to each other, for example 1,2-phenylene, 1,2-naphthylene, 2,3-naphthylene and 1,8-naphthylene. Preferred alkyl substituents in formula I are those with 1-4 carbon atoms and chlorine is the preferred halogen substituent.

Examples of preferred catalysts of formula I are N-hydroxysuccinimide, N-hydroxymaleic acid imide, N-hydroxyphthalimide, N-hydroxy-2,3-naphthalenedicarboxylic acid imide and the compounds substituted with C$_1$-C$_4$-alkyl and/or chlorine which are derived therefrom, such as N-hydroxy-t-butylmaleic acid imide, N-hydroxy-3,4,5,6-tetrachlorophthalimide and the like. Preferably, A-B in formula I above stands for CH=CH. 1,2-phenylene or a group substituted with C$_1$-C$_4$-alkyl and/or chlorine which is derived therefrom. The especially preferred catalyst is N-hydroxyphthalimide.

According to the inventive process isoprenoid having an allylic hydrogen atom, i.e. isoprenoids which possess a methyl, methylene or methyne group on a C—C double bond are oxidized.

Under the term "isoprenoid" in the technical literature there are classified compounds which in a more or less apparent manner might be obtainable by combining isoprene units. The term isoprenoid therefore embraces sub-groups such as hemiterpenes terpenes sesquiterpenes diterpenes, sesterterpenes, triterpenes, tetraterpenes, carotinoids, steroids and the like. The terpenes, sesquiterpenes, diterpenes, sesterterpenes, triterpenes and tetraterpenes as well as similar compounds with an isoprenoid structural basis are also classified under the term terpenoids. With respect to the definition of the terms carotinoid, isoprenoid, steroid, terpenoid etc, reference is made to Rompps Chemie Lexikon, especially volume 1, 609 (1979), volume 3, 1965 (1983), volume 5, 3336 (1975) and volume 6, 3504 (1977).

The term "Isoprenoids" is a group name for natural substances which may have been derived, in a more or less obvious manner, from the assembly of isoprene units. Substances with 10, 15, 20, 30 and 40 carbon atoms in the empirical formula are more predominant than others in nature and moreover have methyl substituents in very specific positions of their structure, prompting Ruzicka to formulate the "isoprene rule". Accordingly, isoprenoids include the compounds described in greater detail under specific entries, namely hemiterpenes, terpenes, iridoids, sesqui-, di-, sester- and triterpenes, carotenoids, steroids and in particular naturally occurring substances, a prime example being dolichol. However, synthetic polyisoprene, for example, is generally not considered an isoprenois, but natural rubber, balata and gutta percha are. Many non-isoprenoid natural substances have isoprenoids in their side chains; examples: tocopherols, vitamin K, phyllo-, plasto-, and ubiquinone (multiprenyl chains), chlorophyll (phytyl chain). Just as the biogenesis of the isoprenoids has been elucidated (see mevalonic acid), so has the degradation pathway of specific isoprenoids, e.g. through microrganisms (Seubert and Fass, Biochem. Z. 341 (1965).

The above terms isoprenoid, steroid, terpenoid, terpene, sesquiterpene etc embrace not only hydrocarbons with an isoprenoid structural basis, but also alcohols, aldehydes, ketones and esters derived therefrom. Preferred starting materials in the inventive process are the isoprenoid hydrocarbons and the alcohols or esterified alcohols derived therefrom i.e. compounds with a group RO— in which R denotes hydrogen or acyl.

The term "acyl" signifies in the scope of the present invention usual acyl residues, especially alkanoyl residues and aroyl residues such as formyl, acetyl, propionyl, butyryl, benzoyl and the like. Acyl residues with a maximum of 11 carbon atoms are preferred. Especially preferred are acyl residues with a maximum of 7 carbon atoms, particularly acetyl.

Preferred starting materials in the process in accordance with the invention are the steroids, terpenes and sesquiterpenes which have at least one allylic hydrogen atom. Preferred examples of such compounds are cholesterol (5-cholesten-3β-ol) and cholesterol esters (3β-acyloxy-5-cholestenes), α-pinene, β-pinene, limonene, citronellol and citronellyl esters, linalool and linalyl esters, dehydrolinalool and dehydrolinalyl esters, α-terpinene, α-cedrene, valencene and isolongifolene.

The oxidation in accordance with the invention is effected radical-wise and is therefore essentially influenced by the stability of the radicals which are formed as intermediates. In this connection, allyl rearrangements can occur under certain circumstances. However, the course of the reaction and the type of product which is formed are determined according to rules concerning the stability of radicals which are known to the person skilled in the art.

An inert ester or an inert ketone is conveniently used as the solvent for the oxidation in accordance with the invention. Mixtures of these solvents with one another or with other inert organic solvents can also be used if desired. Preferred esters and ketones are those with a maximum of 8 carbon atoms and especially those with a maximum of 6 carbon atoms. A preferred group of esters comprises the alkyl alkanoates, especially the alkyl acetates such as methyl acetate, ethyl acetate, n-propyl acetate, isopropyl acetate, n-butyl acetate, isobutyl acetate and t-butyl acetate. Preferred ketones are the alkanones and cycloalkanones such as acetone, methyl ethyl ketone, methyl isobutyl ketone and cyclohexanone. Especially preferred solvents are ethyl acetate, acetone and particularly methyl isobutyl ketone and cyclohexanone.

Compounds with basic groups or "acidic" hydrogen can lead to ionic reactions on the catalyst and therefore to partial or complete inactivation of the catalyst. The reaction mixture should therefore advantageously contain no basic compounds with a $pK_b$ value below about 9, preferably no basic compounds with a $pK_b$ value below about 11. Further, the reaction mixture should advantageously contain no compounds with "acidic" hydrogen whose $pK_a$ value lies below about 13, preferably no compounds whose $pK_a$ value lies below about 15. The above $pK_a$ and $pK_b$ values relate to aqueous solutions of the respective compounds at 25° C. The starting materials, catalysts and solvents which are used in accordance with the invention have no interfering acidic or basic groups. For example, alcohols can also be reacted according to the process in accordance with the invention. However, it is generally preferred to use alcohols in esterified form.

The remaining reaction conditions such as temperature, pressure, oxygen concentration of the gas which is used, educt concentration and amount of catalyst are not critical.

The oxidation in accordance with the invention is preferably carried out at atmospheric pressure and at a temperature of about 10°–125° C. particularly at about 20°–80° C.

The oxygen content of the gas which is used can be varied in wide limits and generally amounts to about 10–100 vol. %, preferably about 20–50 vol. %. Pure oxygen or a mixture of oxygen and an inert gas (e.g. nitrogen, argon) is conveniently used as the oxidation agent. The use of air or air enriched with oxygen is especially preferred.

The optimal educt concentration depends on the educt which is used, on the solvent, on the temperature and the like, but it generally lies in a range of about 0.005–0.3 mol/l.

The catalyst is generally used in an amount of about 0.1–1 mol equivalent, preferably about 0.25–1 mol equivalent, based on the amount of educt. Higher amounts of catalyst are, however, not detrimental. Lower amounts of catalyst are likewise possible, but can, however, lead to a slowing down of the reaction.

The reaction time can vary according to the conditions. If desired, the course of the reaction can be accelerated by a) heating the reacting mixture, for example to a temperature of about 50°–100° C., b) adding a small amount of a radical former and heating to its decomposition temperature or to a higher temperature, c) irradiating with ultraviolet light, for example at about 10°–40° C., or d) increasing the amount of catalyst. The addition of a radical starter and heating to at least its decomposition temperature is especially preferred. Usual radical starters such as e.g. dibenzoyl peroxide can be used in this case.

After completion of the oxidation the catalyst can be separated from the reaction mixture in a simple manner, e.g. with the aid of a non-polar solvent, and can be reused. For example, the reaction mixture can be concentrated, then treated with a non-polar solvent and the catalyst can be crystallized-out. Preferably, however, the solvent which is used in the oxidation is removed completely by evaporation and the residue is taken up in a non-polar solvent, in which case the catalyst remains behind as an insoluble residue. Examples of suitable non-polar solvents are hydrocarbons and non-polar chlorinated hydrocarbons such as hexane, tetrachloromethane and the like.

The allylic oxidation of isoprenoids in accordance with the invention generally leads to hydroperoxides. In the oxidation of compounds which correspond to a dihydro derivative of an aromatic compound, for example in the case of compounds with a cyclohexa-1,3-diene ring, there are, however, generally obtained the corresponding aromatic compounds, i.e. the novel oxidation in this case results in a dehydrogenation.

The oxidation products obtained can be separated from the reaction mixture according to known methods. If desired, hydroperoxides obtained can be further reacted to give alcohols or carbonyl compounds. A purification of the hydroperoxides is not necessary in these cases.

The reduction of the hydroperoxides to alcohols can be carried out according to methods known in the art, e.g. with an alkali metal sulphite in water, with an alkali metal iodide in glacial acetic acid, with sodium borohydride in a protic solvent or with triphenylphospine in a aromatic solvent or by catalytic hydrogenation.

Primary and secondary hydroperoxides can be converted into the corresponding carbonyl compounds (aldehydes or ketones) by water cleavage. Suitable dehydrating agents are fundamentally known to the person skilled in the art. However, the dehydration is preferably carried out with copper-(I) chloride, copper-(II) chloride or a carboxylic acid anhydride such as acetic anhydride, phthalic acid anhydride and the like in pyridine. When a carboxylic acid anhydride is used compounds which have a hydroxy group are simultaneously esterified. If desired, the ester group can subsequently be cleaved off according to known methods (e.g. by saponification with sodium hydroxide solution).

The following reactions are examples of especially preferred conversions according to the process in accordance with the invention:

a) Oxidation of cholesterol or cholesterol esters to the 7-hydroperoxy derivative and, if desired, dehydration of the hydroperoxide to 7-ketocholesterol or 7-ketocholesterol esters

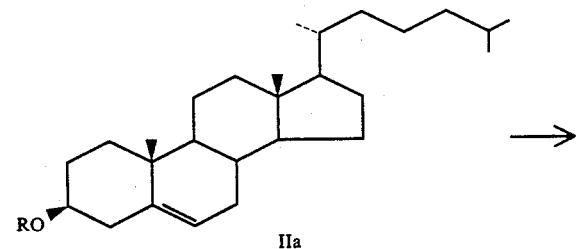

b) Oxidation of α-pinene to the hydroperoxy derivative and, if desired, dehydration of the hydroperoxide to verbenone

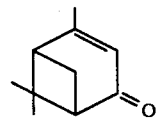

c) Oxidation of citronellol or citronellyl esters and, if desired, reduction of the resulting hydroperoxide to 3,7-dimethyl-5-octene-1,7-diol or a half ester thereof

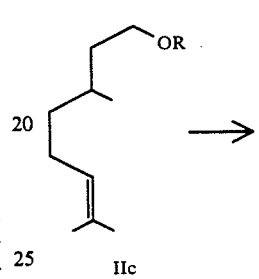

d) Oxidation of linalool, dehydrolinalool or an ester thereof and, if desired, reduction of the resulting hydroperoxide to 2,6-dimethyl-3,7-octadien-2,6-diol, 2,6-dimethyl-3-octen-7-yne-2,6-diol or a half ester thereof

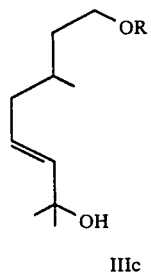

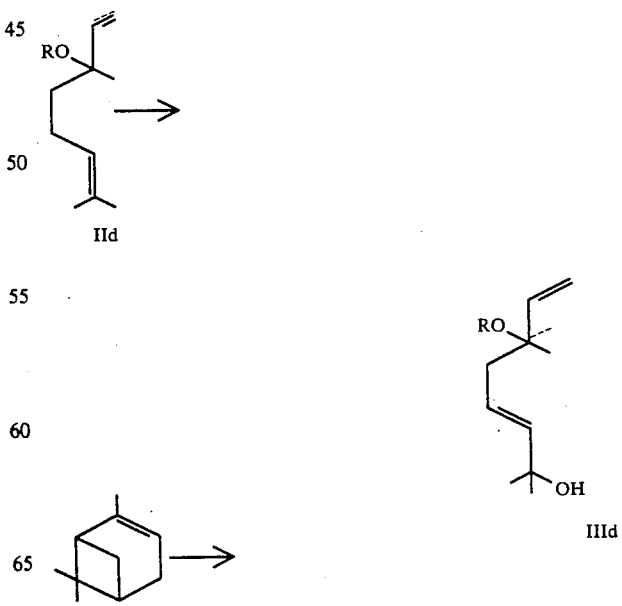

e) Oxidation (dehydrogenation) of α-terpinene to p-cymene

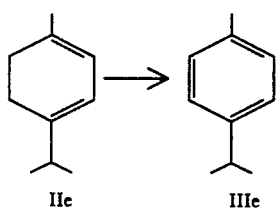

f) Oxidation of α-cedrene and, if desired, dehydration of the resulting hydroperoxide to cedrenone

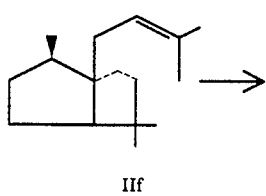

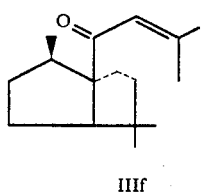

g) Oxidation of valencene and, if desired, dehydration of the resulting hydroperoxide to nootkatone

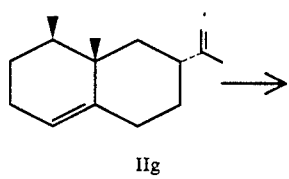

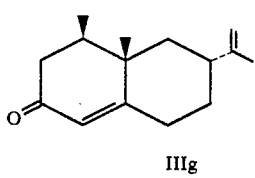

h) Oxidation of isolongifolene and, if desired, dehydration of the resulting hydroperoxide to isolongifolenone

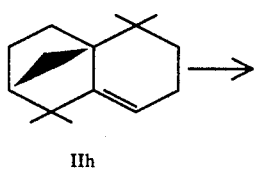

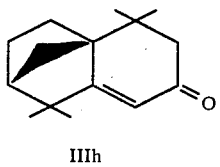

In formulae IIa, IIIa, IIc, IIIc, IId and IIId R signifies hydrogen or acyl, preferably one of the acyl groups mentioned above. In formulae IId and IIId the symbol - - - denotes an optional additional C—C bond. In formulae IIa, IIIa, IIf, IIIf, IIg, IIIg, IIh and IIIh the symbol ▽ signifies that the respective bond lies above the plane of the drawing and the symbol ▲ signifies that the respective bond lies below the plane of the drawing. In the case of formulae IIg and IIIg the latter symbol signifies that the isopropenyl residue lies below the plane of the drawing.

The process in accordance with the invention is illustrated in more detail by the following Examples.

Example 1

A solution of 16.3 g (0.1 mol) of N-hydroxyphthalimide in 350 ml of acetone was heated to boiling in a sulphonation flask equipped with a gasification stirrer, a thermometer and a reflux condenser and treated in succession with 42.8 g (0.1 mol) of cholesterol acetate and 0.16 g (0.5 mmol) of dibenzoyl peroxide. Subsequently, a weak stream of compressed ar was conducted into the reaction solution while stirring at reflux temperature for 9 hours. Thereafter, the reaction mixture, cooled to room temperature, was evaporated to dryness on a rotary evaporator (bath temperature 40°-50° C.). The residue was treated with 200 ml of tetrachloromethane and heated to 40° C. The resulting finely crystalline precipitate was filtered off under suction after cooling the reaction mixture to room temperature, washed with 50 ml of tetrachloromethane and dried in a water-jet vacuum at 80° C. for 4 hours. There were thus recovered 16.0 g (98.2%) of N-hydroxyphthalimide.

The filtrate was evaporated on a rotary evaporator and the oily residue was taken up in 200 ml of pyridine while stirring at 50° C. This solution was cooled to 5°-10° C. and treated with 20 ml of acetic anhydride while cooling. The mixture was left to stand at room temperature overnight and then concentrated on a rotary evaporator. The residue was treated with 100 ml of methanol and stirred at 50° C. The resulting suspension was cooled in an ice-bath for 1 hour and then suction filtered. The crystals were washed on the suction filter with 50 ml of methanol and then dried at 80° C. in a water-jet vacuum for 4 hours. There were thus obtained 32.6 g (73.8%) of 7-ketocholesterol acetate as slightly yellow crystals with m.p. 151°-154° C. This crude product was dissolved in 150 ml of acetone by boiling at reflux. The solution was concentrated to 80 ml and cooled in an ice-bath for 3 hours. The resulting crystallizate was filtered off under suction, washed on the suction filter with 20 ml of acetone and dried at room temperature in a water-jet vacuum for 4 hours. There were obtained 29.8 g (67.4%) of 7-ketocholesterol acetate in the form of colourless crystals with m.p. 156°-159° C.

Example 2

6.1 g (0.037 mol) of N-hydroxyphthalimide were dissolved in 175 ml of isobutyl methyl ketone at 54° C. The solution was treated with 16 g (0.037 mol) of cholesterol acetate and 0.06 g (0.25 mmol) of dibenzoyl peroxide. Subsequently, air (250 ml/min.) was conducted into the reaction solution at 54° C. and while stirring intensively for about 9 hours. After completion of the oxidation the reaction mixture, cooled to room temperature, was evaporated to dryness. In order to recover the N-hydroxyphthalimide, the residue was treated with 75 ml of tetrachloromethane and the mixture was stirred at 40° C. for 1 hour and then filtered at 20° C. In this manner there were recovered 92% of the N-hydroxyphthalimide.

The filtrate was evaporated and the residue was treated with 75 ml of pyridine while stirring. Subsequently, the mixture was treated at 5°–10° C. with 7.5 ml of acetic anhydride, left to stand at room temperature overnight and then evaporated. The residue was treated with 40 ml of methanol. The mixture was stirred at 50° C. for 15 minutes and then in an ice-bath for 1 hour and subsequently filtered. There was obtained crystalline 7-ketocholesterol acetate (purity 97%) in a yield of 72%.

In analogous experiments 175 ml of ethyl methyl ketone. 175 ml of diethyl ketone or 175 ml of cyclohexanone were used as the solvent in place of 175 ml of isobutyl methyl ketone. Under the same reaction conditions and using the same working-up the yield of isolated 7-ketocholesterol acetate amounted to 66% when ethyl methyl ketone was used, to 68% when diethyl ketone was used and to 80% when cyclohexanone was used.

Example 3

The experiments compiled in Table 1 were carried out according to the method described in Example 2. Cholesterol was used as the educt in experiment (a) and cholesterol acetate was used as the educt in the remaining experiments. The conversion of the hydroperoxide into the ketone by water cleavage was carried out with acetic anhydride in pyridine, with the exception of experiment (d) in which the water cleavage was carried out with $CuCl_2.2H_2O$ in pyridine. As in experiment (a) the hydroxy group was simultaneously esterified in the water cleavage with acetic anhydride in pyridine, 7-ketocholesterol acetate was obtained as the end product in all experiments. In Table 1 T signifies the reaction temperature and t signifies the reaction time for the oxidation with air. The yields of 7-ketocholesterol acetate which are given relate to reacted educt. The reaction conditions were generally not optimized.

N-hydroxyphthalimide by filtration the filtrate was evaporated to dryness.

The residue was taken up in 25 ml of pyridine and the cooled solution was treated with 2.5 ml of acetic anhydride. After 16 hours the reaction mixture was partitioned in water/diethyl ether. The organic phase was separated, dried and evaporated. The residual crude product (2.0 g) was chromatographed on silica gel with hexane/diethyl ether (vol. 7:3) and then distilled. There were obtained 1.3 g of (−)-verbenone in a purity of 77.7%; yield 51% based on reacted (−)-α-pinene.

Example 5

Air (250 ml/min.) was conducted into a mixture of 6.45 g of citronellol acetate (purity 92%), 4.8 g of N-hydroxyphthalimide and 105 ml of acetone while stirring intensively at reflux. After 6 hours 81.7% of the citronellol acetate had reacted. The oxidation was interrupted and the solvent wa removed by evaporation. The residue was taken up in tetrachloromethane/hexane (vol. 1:1). 4.67 g of N-hydroxyphthalimide could be recovered by filtration. The filtrate was evaporated. The residual oil was chromatographed on silica gel with dichloromethane/acetone (vol. 95:5). There were thus obtained 4.46 g of (E)-7-hydroperoxy-3,7-dimethyl-5-octen-1-yl acetate in a purity of 95%; $n_D^{23} = 1.460$; yield 75.2% based on reacted citronellol acetate.

Example 6

Air (250 ml/min.) was conducted into a mixture of 10 g of linalool acetate (purity 95%). 8.3 g of N-hydroxyphthalimide. 0.81 g of dibenzoyl peroxide and 300 ml of ethyl acetate while stirring intensively at reflux for 10 hours. Thereafter, the solvent was removed by evaporation and the residue was taken up in 150 ml of tetrachloromethane. The mixture was stirred at room temperature for 1.5 hours and then filtered. There were thus recovered 7.4 g of N-hydroxyphthalimide. The filtrate was evaporated, whereby 13.83 g of a yellowish oil remained behind. 2.0 g of the resulting, oily residue were chromatographed on silica gel with cyclohex-

TABLE 1

| Experiment | Catalyst | Activator | Solvent | T | t | Conversion | Yield |
|---|---|---|---|---|---|---|---|
| (a) | NHPI | DBP | $CH_3COCH_3$ | 52–53° C. | 9 h | 100% | 66% |
| (b) | NHPI | — | $CH_3COCH_3$ | 52–53° C. | 24 h | 100% | 75.3% |
| (c) | NHPI | — | $CH_3COO(CH_2)_3CH_3$ | 118–124° C. | 2 h | 100% | 67.4% |
| (d) | NHPI | hν | $CH_3COCH_3$ | 14° C. | 8 h | 100% | 45% |
| (e) | NHPI | DBP | $CH_3COOCH_2CH_3$ | 73–74° C. | 2 h | 94.2% | 68.2% |
| (f) | N-Hydroxymaleic acid imide | DBP | $CH_3COOCH_2CH_3$ | 73–74° C. | 6 h | 70.5% | 91.4% |
| (g) | N-Hydroxy-t-butylmaleic acid imide | DBP | $CH_3COOCH_2CH_3$ | 73–74° C. | 6 h | 95.9% | 70.2% |
| (h) | N-Hydroxysuccinimide | DBP | $CH_3COOCH_2CH_3$ | 73–74° C. | 6 h | 62.0% | 65.1% |
| (i) | N-Hydroxy-3,4,5,6-tetrachlorophthalimide | DBP | $CH_3COOCH_2CH_3$ | 73–74° C. | 6 h | 100% | 61.3% |
| (j) | N-Hydroxy-2,3-naphthalenedicarboxylic acid imide | DBP | $CH_3COCH_3$ | 52–53° C. | 24 h | 95.5% | 53.2% |

NHPI = N-Hydroxyphthalimide
DBP = Dibenzoyl peroxide
Hν = Irradiation with a mercury vapour lamp (150 W)

Example 4

A stream of air (16 l/h) was conducted into a mixture of 4.1 g of (−)-α-pinene. 4.8 g of N-hydroxyphthalimide, 0.05 g of dibenzoyl peroxide (containing 20–25% water) and 105 ml of isobutyl methyl ketone while stirring at 54°–55° C. 44% of the educt had reacted after 6 hours. The oxidation was interrupted and the solvent was removed by evaporation. The residue was taken up in hexane/diethyl ether (vol. 1:1). After separating the ane/diethyl ether (vol. 1:1). There was thus obtained 0.90 g of 2-hydroperoxy-2,6-dimethyl-3,7-octadien-6-yl acetate as a colourless oil. The compound was characterized by infra-red, nuclear resonance and mass spectroscopy.

The remaining 11.83 g of the oily residue were dissolved in 250 ml of ethanol. The solution was treated with 15.3 g of sodium iodide and 5.85 ml of glacial acetic acid, stirred at room temperature for 3 hours and then evaporated. The residue was dissolved in 200 ml of dichloromethane and the solution was washed once with 200 ml of 20% sodium thiosulphate solution and twice with 125 ml of 20% sodium thiosulphate solution each time. The aqueous phases were back-extracted twice with 125 ml of dichloromethane each time. The organic phases were dried over sodium sulphate, filtered and evaporated.

The resulting oily residue (10.49 g) was dissolved in 100 ml of methanol. The solution was treated with 4.5 g of potassium carbonate and stirred at 40° C. for 8 hours and subsequently at room temperature for a further 16 hours. Thereafter, the reaction mixture was evaporated and the residue was treated with 150 ml of diethyl ether. The mixture was stirred at room temperature for 30 minutes and filtered. The red oily residue (6.26 g) obtained after evaporation of the filtrate was chromatographed on silica gel with dichloromethane/ethyl acetate (vol. 1:1). There were thus isolated 3.27 g of 2,6-dimethyl-3,7-octadiene-2,6-diol in the form of a reddish oil. ($n_D^{23} = 1.474$); yield 37.7% based on linalool acetate. The remaining fractions, which to some extent also contained product, were not worked-up.

Example 7

The educts set forth in Table 2 were oxidized with air in the presence of N-hydroxyphthalimide according to the method described in Examples 1-6. All experiments were carried out in acetone at the reflux temperature of the reaction mixture and with the addition of dibenzoyl peroxide.

Experiment (e) gave p-cymene as the oxidation product. In experiments (a)-(d) there were obtained as oxidation products hydroperoxides which were reacted further with acetic anhydride in pyridine in an analogous manner to Examples 1-4 to give the ketones set forth in Table 2.

In Table 2 t signifies the reaction time for the oxidation with air. The yields of product which are given are based on reacted educt. The reaction conditions were not optimized.

TABLE 2

| Experiment | Educt | t | Conversion | Yield | Product |
|---|---|---|---|---|---|
| (a) | α-Pinene | 13 h | 92% | 36.3% | Verbenone |
| (b) | Valencene | 24 h | 94.8% | 55.6% | Nootkatone |
| (c) | Isolongifolene | 35 h | 100% | 68% | Isolongifolenone |
| (d) | α-Cedrene | 16.5 h | 100% | 46.1% | Cedrenone |
| (e) | α-Terpinene | 8.5 h | 100% | 74% | P-Cymene |

What is claimed is:

1. A process for the catalytic oxidation of an isoprenoid which has at least one allylic hydrogen atom, which process comprises oxidizing said isoprenoid with oxygen or a gas which contains oxygen, in an inert solvent, in the absence of a basic compound or a compound with an acidic hydrogen and in the presence of a N-hydroxydicarboxylic acid imide of the formula

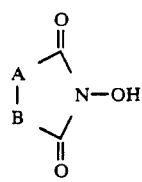

wherein A-B stands for $CH_2-CH_2$, $CH=CH$, a diradical group which is derived from an aromatic hydrocarbon whereby positions of diradicals of the group are ortho- or peri-position to each other, or a group which is derived from the diradical group having at least one hydrogen atom unsubstituted or substituted with alkyl or halogen, to produce a hydroperoxide.

2. A process according to claim 1 comprising: selecting said isoprenoid as a cholesterol, a cholesterol ester, α-pinene, β-pinene, limonene, citronellol, citronellyl esters linalool, linalyl esters, dehydrolinalool, dehydrolinalyl esters, α-terpinene, valencene, α-cedrene or isolongifolene.

3. A process according to claim 2, wherein said selecting step comprises: selecting said isoprenoid as a cholesterol or a cholesterol ester.

4. A process according to claim 2, wherein said selecting step comprises selecting said isoprenoid as an α-pinene, valencene, α-cedrene or isolongifolene.

5. A process according to claim 2, wherein A-B is $CH=CH$, 1,2-phenylene or a group which is derived from one of these groups and which is substituted with $C_1-C_4$-alkyl or chlorine.

6. A process according to claim 2 comprising: selecting said acid imide from the group consisting of N-hydroxysuccinimide, N-hydroxymaleic acid imide, N-hydroxyphthalimide, N-hydroxy-2,3-naphthalenedicarboxylic acid imide, N-hydroxy-t-butylmaleic acid imide or N-hydroxy-3,4,5,6-tetrachlorophthalimide.

7. A process according to claim 6, wherein said oxidizing is carried out in the presence of N-hydroxyphthalimide.

8. A process according to claim 1, comprising: selecting said inert solvent as an alkanone, a cycloalkanone or an alkyl alkanoate with a maximum of 8 carbon atoms.

9. A process according to claim 8, comprising: selecting said inert solvent as methyl isobutyl ketone, acetone, cyclohexanone or ethyl acetate.

10. A process according to claim 1, wherein said oxidizing comprises: selecting air or air enriched with oxygen to be used as an oxidation agent.

11. A process according to claim 1, wherein said oxidizing comprises: adding a sufficient amount of a radical former to be used as a radical started and heating a reaction mixture to at least the decomposition temperature of the radical starter.

* * * * *